United States Patent [19]

Holtkamp

[11] Plant 4,351

[45] Dec. 19, 1978

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 880,211

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Beall & Jeffery

[57] ABSTRACT

An African violet named Montana which is a mutation of Gigi, disclosed in U.S. Plant Pat. No. 3,146. Montana has white flowers with blue tinging in the centers. The flowers are carried on strong, upright flower stems, and the plant is fast growing and has a compact growing habit. Initial flowering is 7–8 weeks after potting. Montana has green leaves with smooth edges, the leaves having a hairy and velvety texture.

1 Drawing Figure

The present invention comprises a new and distinct cultivar of African violet plant, botanically known as *Saintpaulia ionantha,* and referred to by the cultivar name Montana. The new cultivar, referred to during the discover and selection process by the designation IX/12, 83/77 is a mutation of the cultivar Gigi, disclosed in U.S. Plant Pat. No. 3,146, granted May 2, 1972, to Hermann Holtkamp. Montana is characterized by its non-dropping flowers which sit on short, slightly curved peduncles which are carried on straight, strong flower stems. There are 5–7 single flowers per stem when the plant blooms for the first time. Montana is principally distinguished from the parent cultivar Gigi by its white flower color with a tinging of blue in the center of the flower, the shape of its leaves and its strong, upright stems. The flowers in Gigi are white with pronounced blue edges, the leaves have wavy edges, and the stems are not as strong or upright.

Montana was discovered as a flowering plant in a block of plants of the parent cultivar in a controlled environment in Isselburg, Rhineland, Germany, and selections were subsequently made. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Montana, which in combination distinguish this African violet as a new and distinct cultivar:

1. Strong, straight flower stems.
2. There are 5–7 flower stems when the plant blooms for the first time.
3. There are 5–6 flowers on each flower stem.
4. The flowers are snowy white, with light blue centers.
5. The leaves are oblong, slightly hairy and velvety, and have relatively smooth edges.

6. The habit is very compact, and the plant is fast growing, with flowering initiating 7–8 weeks after potting.

The accompanying photographic drawing shows a typical specimen plant of the new cultivar. The colors appearing in the photograph are as true as possible with color illustrations of this type.

In the following description, color references are made to the Royal Horticultural Society color chart (RHS), 1966 edition, except where general color terms of ordinary significance are obvious.

Botanical classification: *Saintpaulia ionantha,* Ramat. cv Montana.

Parentage: Mutation of Gigi, U.S. Plant Pat. No. 3,146.

Propagation: The new cultivar holds its distinguishing characteristics through successive propagations by leaf cuttings and by division of shoots.

Plant: From 9 cm. to 11 cm. tall when grown in pots, and approximately 25 cm. in diameter when fully grown.

Leaves.—General Form: Oblong. Diameter: 55 mm. Texture: Soft, velvety, slightly hairy. Veins: Pronounced. Color (upperside): 137 A; the true foliage color is darker than shown in the photograph. Color (underside): 149 D. Petiole: Light green, slightly hairy.

Flowers:

*Buds.*—Diameter 6–7 mm., 145 D.

*Sepals.*—five, 5–6 mm. long. Color: 144 A to 144 B. Calyx: flat funnel. Aspect: Flower stem and receptacle connected. On some flowers, it shows additional small petals. Peduncle: slightly hairy, straight.

Individual flowers:

*Size.*—up to 45 mm. in total flower diameter.

*Color.*—Upperside: 155 D. Underside: 155 D.

*Borne.*—The flower stems carry up to seven flowers.

*Shape and size of petals.*—Two small petals, three large petals; the latter are 20–21 mm. long and 17–18 mm. wide, and the small petals are 15–16 mm. long and 14–15 mm. wide.

*Arrangement.*—On strong, straight flower stems, with up to seven flowers per stem.

*Flowering time.*—7–8 weeks after potting, the first flowers appear; after 9–11 weeks, Montana is in full bloom.

Reproductive organs:

*Stamens.*—Two in number.

*Anthers.*—Four, close together, color 7 A.

*Arrangement.*—Anthers close together, seed-capsule pushes slightly through.

*Filaments.*—3–4 mm. long.

*Styles.*—7–8 mm. long, color 97 D, blue.

*Pollen color.*—7 C.

Roots: Montana has well developed roots; the tips of the roots are white, the older ones white-brownish.

Disease resistance: No disease problems noted to date.

General observations: Montana is an excellent and fast growing African violet with snowy white flowers. The center of the flower and the styles have a blue tint. The flower stems are very strong and straight. The oblong leaves are slightly hairy and velvety, with smooth edges. When blooming for the first time, the plant shows 5–7 strong upright flower stems with 5–7 flowers on short peduncles.

I claim:

1. A new and distinct cultivar of African violet known by the cultivar name Montana and characterized by the combined features of white flowers, having blue centers, the flowers being carried on strong, upright flower stems; fast growing and compact growing habit, with initial flowering being on 5–7 stems 7–8 weeks after potting, and oblong leaves having smooth edges and hairy and velvety texture.

* * * * *

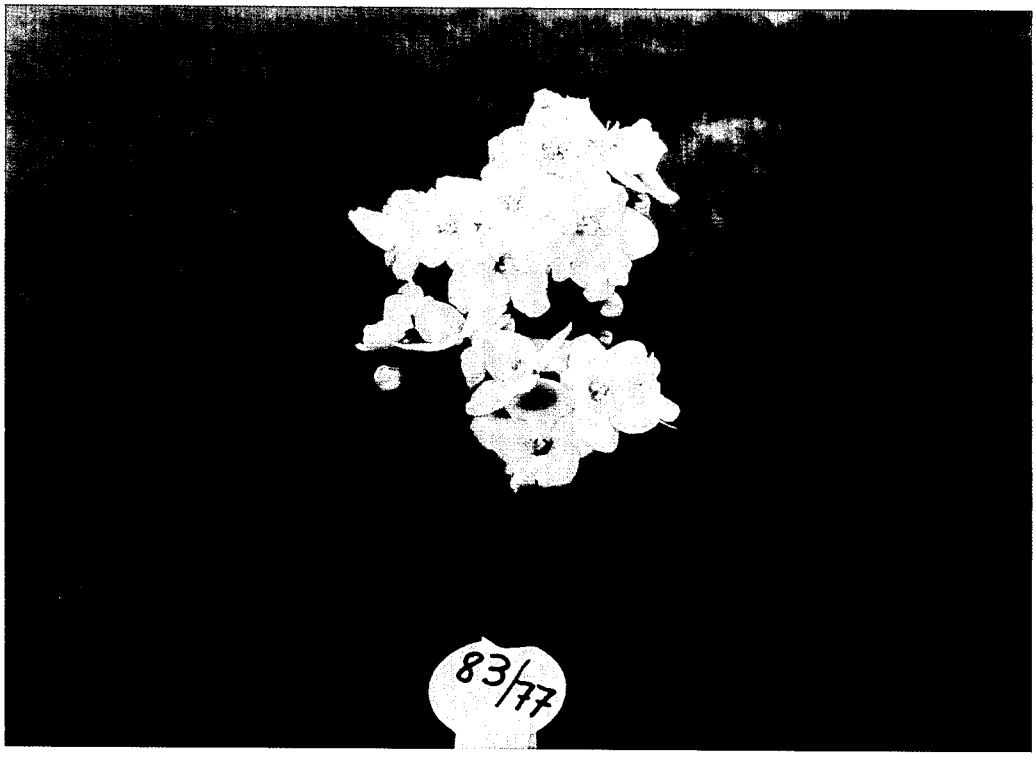
83/77